(12) United States Patent
Kawashima et al.

(10) Patent No.: US 7,812,187 B2
(45) Date of Patent: Oct. 12, 2010

(54) PROCESS FOR PRODUCTION OF FATTY ACID ALKYL ESTER AND PRODUCTION APPARATUS FOR FATTY ACID ALKYL ESTER

(75) Inventors: Ayato Kawashima, Matsuyama (JP);
Hideo Yamamoto, Matsuyama (JP);
Tetsuya Koshikawa, Kyoto (JP)

(73) Assignees: Revo International Inc., Kyoto-shi (JP);
Ehime University, Matsuyama-shi (JP)

( * ) Notice: Subject to any disclaimer, the term of this patent is extended or adjusted under 35 U.S.C. 154(b) by 20 days.

(21) Appl. No.: 12/162,871

(22) PCT Filed: Jan. 26, 2007

(86) PCT No.: PCT/JP2007/000032

§ 371 (c)(1),
(2), (4) Date: Oct. 10, 2008

(87) PCT Pub. No.: WO2007/088702

PCT Pub. Date: Aug. 9, 2007

(65) Prior Publication Data

US 2009/0023938 A1    Jan. 22, 2009

(30) Foreign Application Priority Data

Jan. 31, 2006    (JP) .............................. 2006-021774

(51) Int. Cl.
*C11B 3/00*    (2006.01)
(52) U.S. Cl. .................................................. 554/167
(58) Field of Classification Search .................. 554/167
See application file for complete search history.

(56) References Cited

U.S. PATENT DOCUMENTS 6,288,251 B1    9/2001    Tsuto et al.

(Continued)

FOREIGN PATENT DOCUMENTS

JP    5-286904    11/1993

(Continued)

OTHER PUBLICATIONS

Gryglewicz, Bioresource Technology, vol. 70, pp. 249-253, 1999.*

(Continued)

*Primary Examiner*—Deborah D Carr
(74) *Attorney, Agent, or Firm*—Oblon, Spivak, McClelland, Maier & Neustadt, L.L.P.

(57) ABSTRACT

An object of the present invention is to provide a method for producing an alkyl ester of a fatty acid from a fat or oil, of which main component is a triglyceride, and an alkyl alcohol under mild conditions in a high reaction efficiency, and the alkyl ester of a fatty acid can be effectively utilized as a diesel fuel oil, an industrial raw material or the like, the method further being capable of utilizing on an industrial scale, in which post-treatment steps for removing a catalyst component can be simplified or omitted. For this purpose, the method for producing an alkyl ester of a fatty acid of this invention includes the step of carrying out a transesterification reaction between a fat or oil and an alcohol in the presence of a base catalyst containing calcium oxide, characterized in that the method includes the step of contacting the base catalyst with the alcohol, to carry out an activation treatment thereof in advance of the reaction.

4 Claims, 6 Drawing Sheets

U.S. PATENT DOCUMENTS

2005/0145475 A1    7/2005   Okada et al.

FOREIGN PATENT DOCUMENTS

| JP | 05286904 | * 11/1993 |
| JP | 6-313188 | 11/1994 |
| JP | 2000-109883 | 4/2000 |
| JP | 2001-271090 | 10/2001 |
| JP | 2002-105484 | 4/2002 |
| JP | 2002-241787 | 8/2002 |
| JP | 2004-35873 | 2/2004 |

OTHER PUBLICATIONS

S. Gryglewicz, "Rapeseed oil methyl esters preparation using heterogeneous catalysts", Institue of Chemistry and Technology of Petroleum and Coal, Wroclaw University of Technology, Bioresource Technonolgy, 70, 1999, pp. 249-253.

* cited by examiner

[Figure 1]
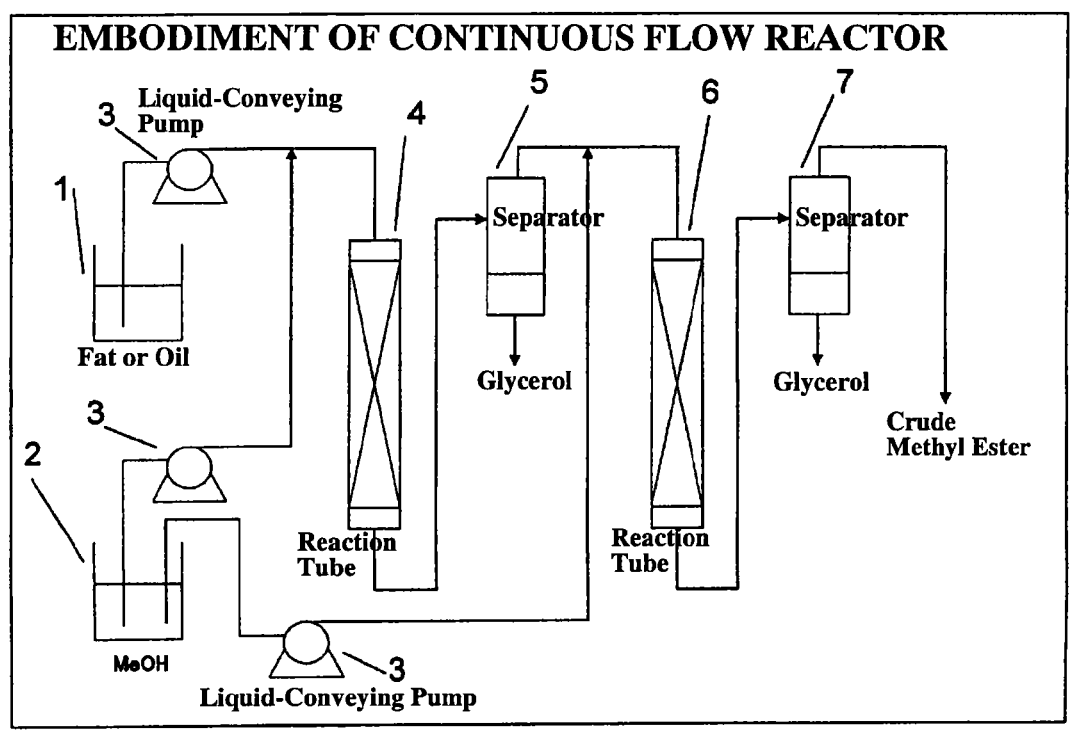

[Figure 2]
EMBODIMENT OF BATCH FLOW REACTOR
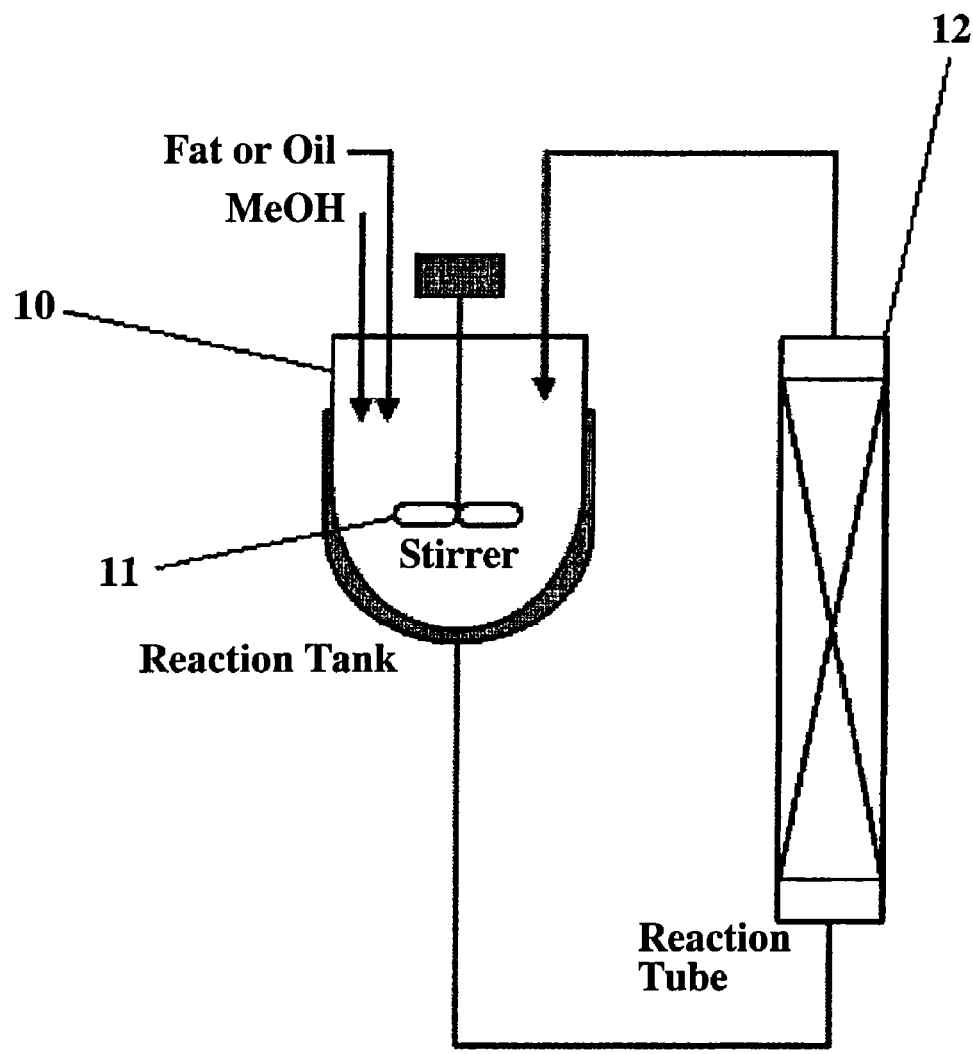

[Figure 3]
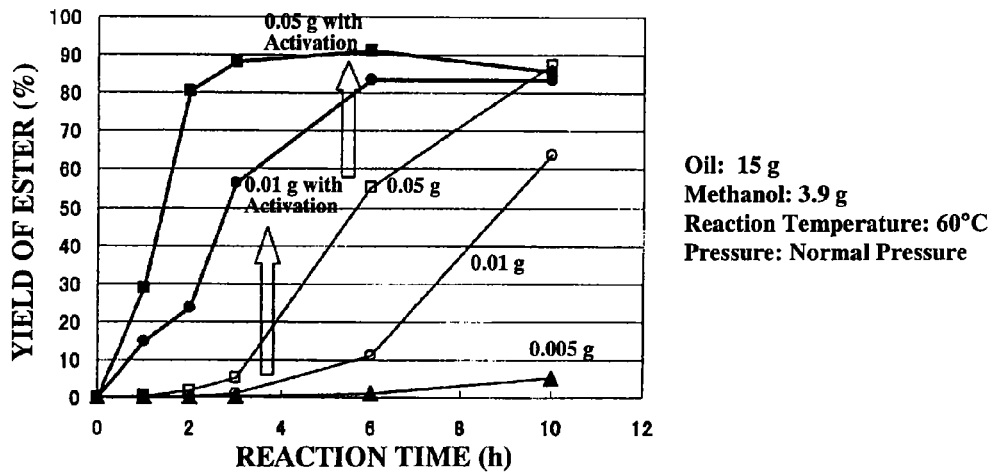
[Figure 4]
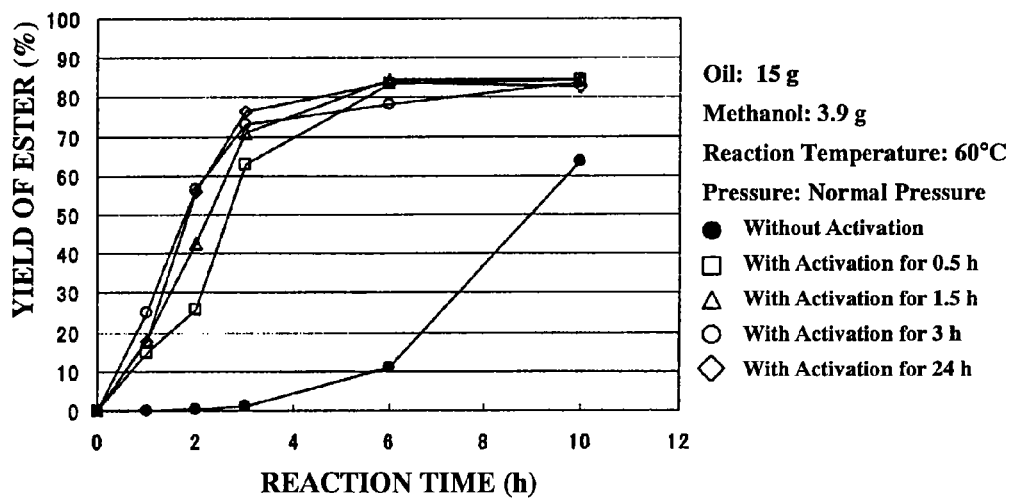

[Figure 5]
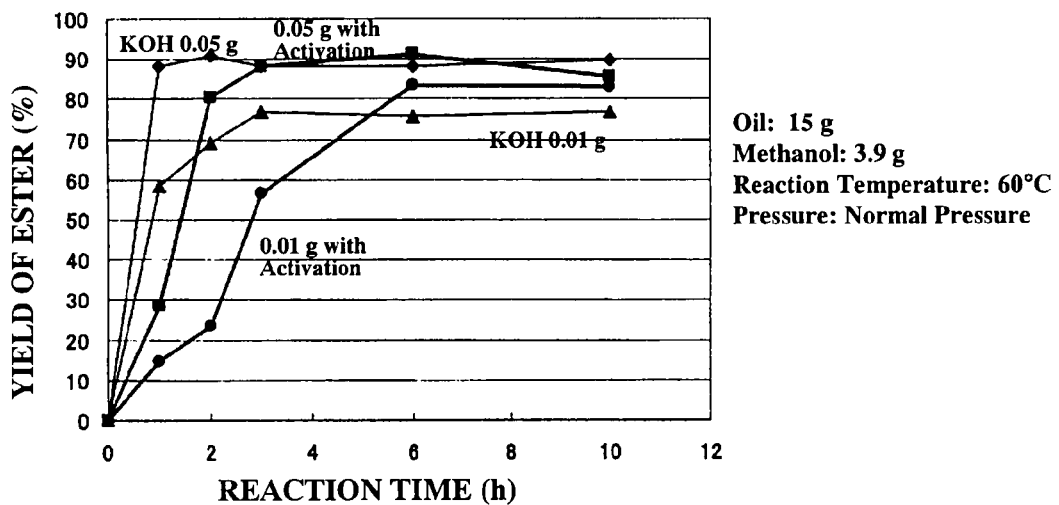
[Figure 6]
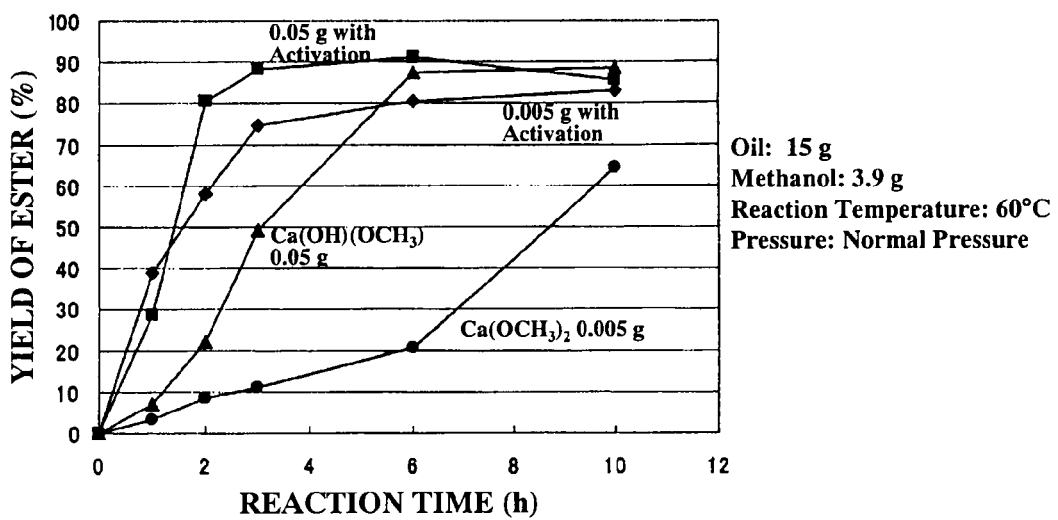

[Figure 7]
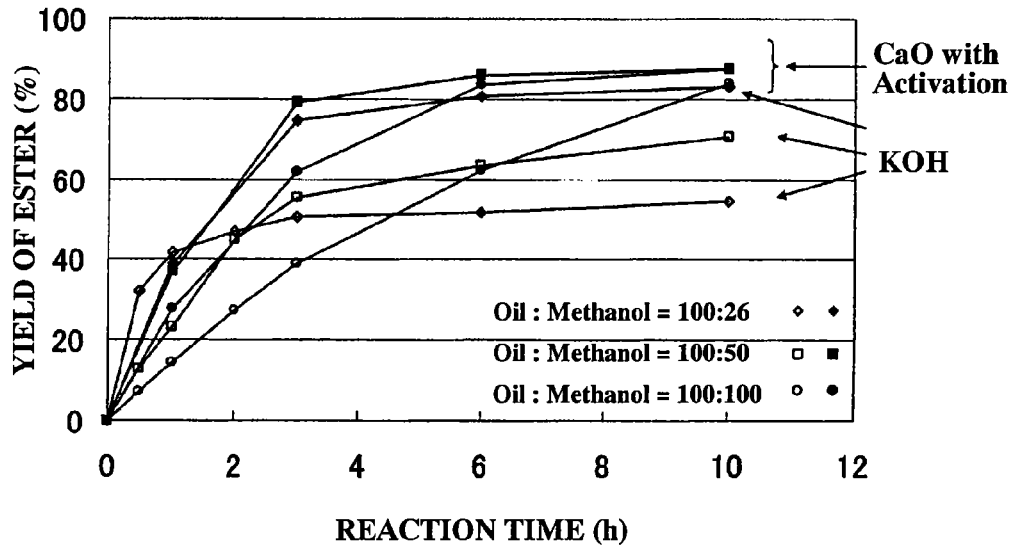
[Figure 8]
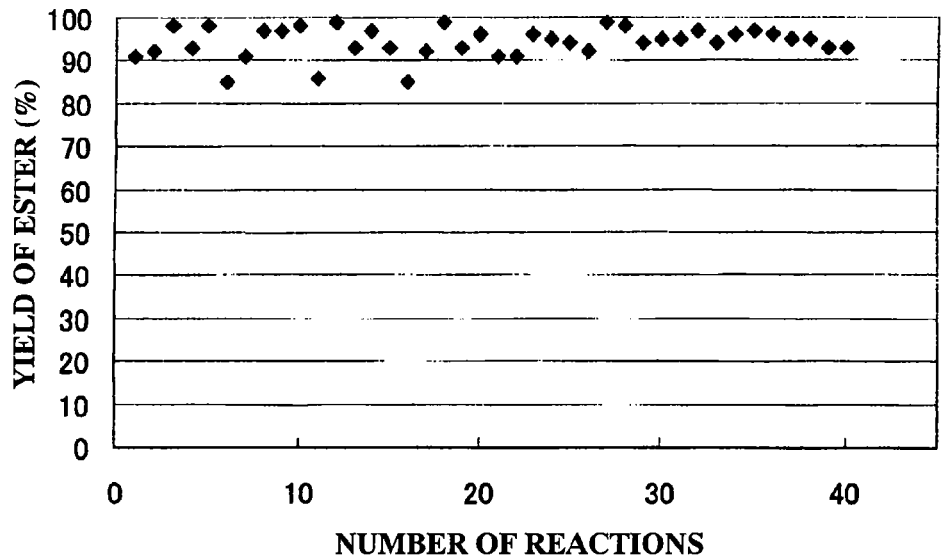
[Figure 9]
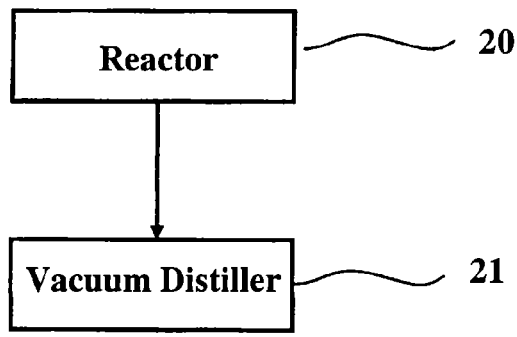

[Figure 10]
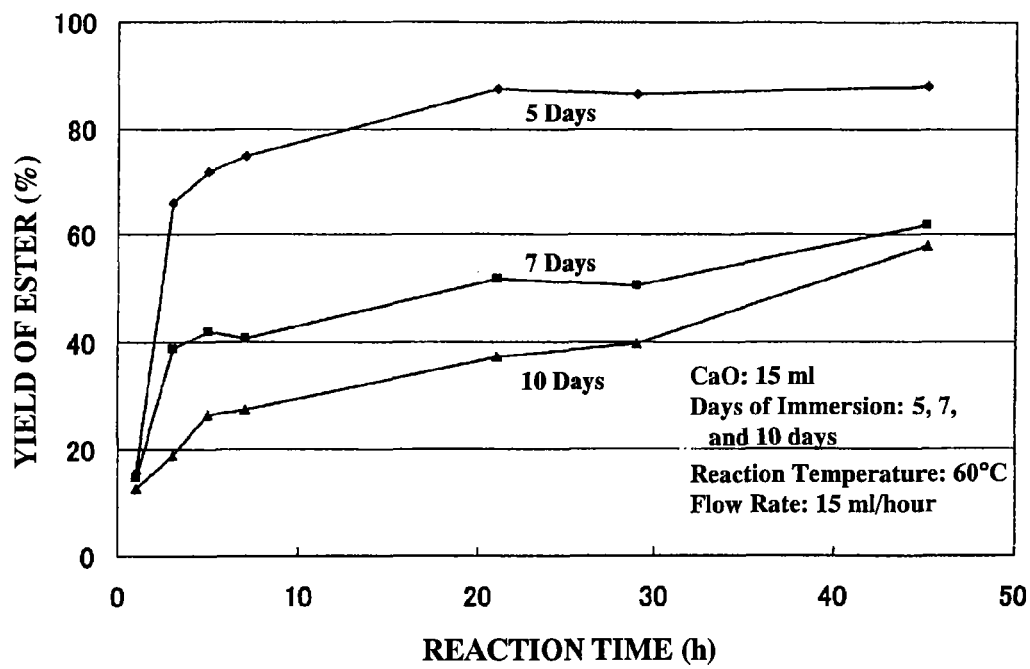
[Figure 11]
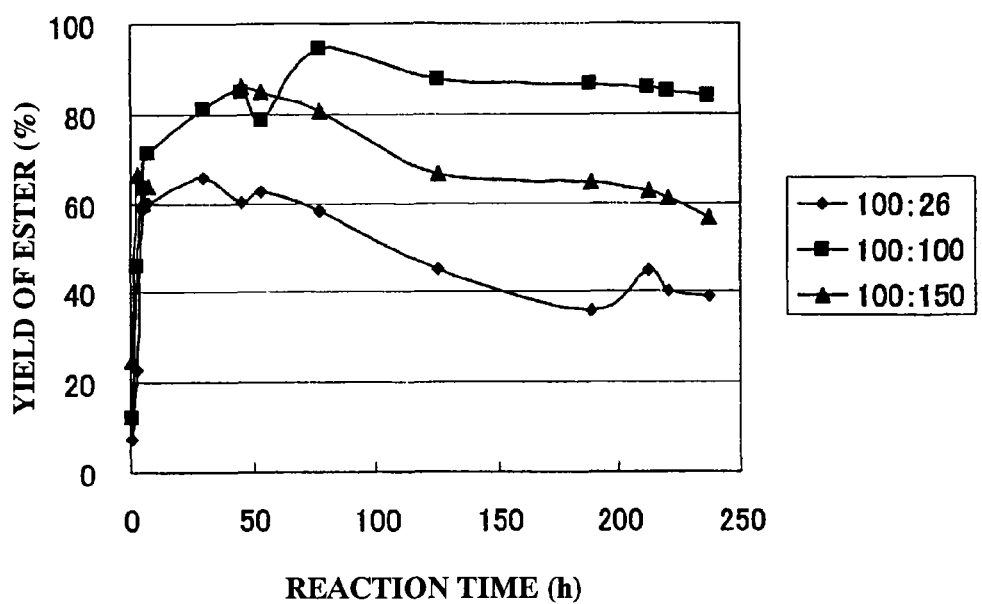

PROCESS FOR PRODUCTION OF FATTY ACID ALKYL ESTER AND PRODUCTION APPARATUS FOR FATTY ACID ALKYL ESTER

TECHNICAL FIELD

The present invention relates to a technical field for producing an alkyl ester of a fatty acid from a fat or oil and an alcohol.

BACKGROUND ART

Alkyl esters of fatty acids, produced between a fat or oil, which is an esterified product of glycerol and a fatty acid, and an alkyl alcohol, not only have been used as industrial raw materials in the fields of cosmetic and medicaments, but also have remarked increasing interests in the recent years as substitute fuels for fuel oils so-called bio-diesel fuels (hereinafter referred to as "BDF"), from the viewpoint of the prevention of global warming and the reduction in environmental loads.

Regarding methods for producing alkyl esters of fatty acids from a triglyceride, a main component of a fat or oil, and an alkyl alcohol by a transesterification reaction, a plural methods have been conventionally known. An industrially most well used method includes the steps of using an alkali metal hydroxide such as potassium hydroxide as a homogeneous catalyst, and carrying out a transesterification reaction near a boiling point of the alcohol in the presence of the catalyst. However, in this this method, there are some disadvantages that the solubility of the catalyst in an organic solvent is high, so that the catalyst is dissolved in an alkyl ester of a fatty acid in a high concentration, whereby a complicated procedure such as rinsing with water is necessitated for the production of a high-quality BDF having a high purity, and a disadvantage in the post-treatment of an alkali-containing wastewater, or the like.

As a method for avoiding these disadvantages, for example, Patent Publication 1 (Japanese Patent Laid-Open No. 2000-109883) discloses a method including the step of reacting an alcohol in a supercritical state and a fat or oil. In this method, a purification procedure, such as removal of a catalyst is not necessitated because the reaction is carried out in the absence of a catalyst. However, since the reaction is carried out under high-temperature and high-pressure conditions, this reaction is not suitable for practical use energetically or process cost-wise.

In addition, there is a method of simplifying the purification procedures by using a fixed catalyst, not a homogeneous catalyst. For example, Patent Publication 2 (Japanese Patent Laid-Open No. Hei 6-313188) discloses a method in which a cationic exchange resin, a composite metal oxide, a solid heteropoly acid or the like is used as a solid acid catalyst. Generally, however, an acid catalyst has a lower activity in the transesterification reaction than a base catalyst; therefore, there are some disadvantages that the reaction must be carried out at a high temperature or for a long period of time, whereby an ether or a degraded product or the like is formed as a by-product.

As a method of using a solid base catalyst as a fixed catalyst, for example, Patent Publication 3 (Japanese Patent Laid-Open No. 2001-271090) discloses a method for producing an ester under conditions within a temperature range of from 90° to 240° C. in the presence of a solid catalyst including calcium hydroxide or calcium oxide; and Patent Publication 4 (Japanese Patent Laid-Open No. 2004-35873) discloses a method for reacting a fat or oil (including a waste oil) and an alcohol with quick lime or dolomitic lime. However, calcium hydroxide or calcium oxide generally has a low activity in the transesterification reaction; therefore, there is a disadvantage that the reaction must be carried out at a high reaction temperature, or for a long reaction time, that a catalyst is needed in a large amount, or the like.

Patent Publication 5 (Japanese Patent Laid-Open No. Hei 5-286904) discloses a method for producing an aromatic ester of an aromatic carboxylic acid including the steps of pre-treating calcium oxide with an alcohol for the reaction to give a catalyst an activated structure of the formula Ca(OH)(OR) . . . , and carrying out a transesterification reaction with an aromatic alcohol using the activated catalyst as a solid base catalyst. However, this Patent Publication 5 is completely silent on the production of an alkyl ester of a fatty acid that can be used as BDF.

Patent Publication 1: Japanese Patent Laid-Open No. 2000-109883
Patent Publication 2: Japanese Patent Laid-Open No. Hei 6-313188
Patent Publication 3: Japanese Patent Laid-Open No. 2001-271090
Patent Publication 4: Japanese Patent Laid-Open No. 2004-35873
Patent Publication 5: Japanese Patent Laid-Open No. Hei 5-286904

DISCLOSURE OF THE INVENTION

Problems to be Solved by the Invention

An object of the present invention is to provide a method for producing an alkyl ester of a fatty acid from a fat or oil, of which main component is a triglyceride, and an alkyl alcohol under mild conditions in a high reaction efficiency, and the alkyl ester of a fatty acid can be effectively utilized as a diesel fuel oil, an industrial raw material or the like, the method further being capable of utilizing on an industrial scale, in which post-treatment steps for removing a catalyst component can be simplified or omitted.

Means to Solve the Problems

In order to solve the above object, the method for producing an alkyl ester of a fatty acid of this invention includes the step of carrying out a transesterification reaction between a fat or oil and an alcohol in the presence of a base catalyst containing calcium oxide, characterized in that the method includes the step of contacting the base catalyst with the alcohol, to carry out an activation treatment thereof in advance of the reaction. In a case where a powdery base catalyst is used, it is preferable that the activation treatment includes the step of stirring this base catalyst in methanol for 15 minutes to 5 hours. On the other hand, in a case where a granular base catalyst is used in a reaction using a tubular reactor or the like, it is preferable that the activation treatment includes the step of immersing the granular base catalyst in methanol for 3 to 7 days. In addition, it is preferable that the method includes the steps of mixing the fat or oil and methanol in a weight ratio of from 100:30 to 100:110, and allowing the resulting liquid mixture to flow through a reaction tube filled with the powdery base catalyst containing calcium oxide subjected to the activation treatment by a contact with methanol to carry out the transesterification reaction. Moreover, a vacuum distillation may be carried out at a temperature of 250° C. or less and a pressure of 1330 Pa or less in order to purify the formed alkyl ester of a fatty acid. Further, the apparatus for producing an alkyl ester of a fatty acid of this invention comprises a mixer for mixing a fat or oil and methanol; a reaction tube to be filled with a powdery base catalyst containing calcium oxide subjected to an activation treatment by a contact with methanol, for carrying out a transesterification reaction including the step of allowing the liquid mixture to flow through the reaction tube; a separator for separating glycerol from the reaction mixture; and a vacuum distiller for purifying the formed alkyl ester of a fatty acid.

EFFECTS OF THE INVENTION

This invention has some effects that a catalyst component is hardly dissolved in the formed product, so that an alkyl ester of a fatty acid having a high purity can be produced. Therefore, the produced alkyl ester of a fatty acid is less harmful even when used as a BDF. The invention also has an effect that a purification step is simplified, so that the production cost is lowered. The invention also has an effect that the base catalyst is activated by an alcohol, so that the catalyst has a high synthesizing ability even while being a solid catalyst.

BRIEF DESCRIPTION OF THE DRAWINGS

FIG. 1 A schematic view showing a flow reactor.

FIG. 2 A schematic view showing a batch flow reactor.

FIG. 3 A graph showing the change with time in an yield of an ester, showing a comparison between a base catalyst subjected to an activation treatment and a base catalyst without the activation treatment.

FIG. 4 A graph showing the change with time in an yield of an ester, showing a comparison among different treatment time for activation of the base catalyst.

FIG. 5 A graph showing the change with time in an yield of an ester, showing a comparison between a base catalyst subjected to an activation treatment and potassium hydroxide.

FIG. 6 A graph showing the change with time in an yield of an ester, showing a comparison between a base catalyst subjected to an activation treatment and an alcoholate catalyst.

FIG. 7 A graph showing the change with time in an yield of an ester in EMBODIMENT 2.

FIG. 8 A graph showing a change in catalytic activity by the number of reactions.

FIG. 9 A block diagram showing the constitution of an apparatus for producing an alkyl ester of a fatty acid.

FIG. 10 A graph showing the change with time in an yield of an ester in EMBODIMENT 5.

FIG. 11 A graph showing the change with time in an yield of an ester, showing a comparison among different ratios of a fat or oil to methanol.

EXPLANATION OF NUMERALS 1. fat or oil tank
2. methanol tank
3. liquid-conveying pump
4. first reaction tube
5. first separator
6. second reaction tube
7. second separator
10. reaction vessel
11. stirrer
12 reaction tube

BEST MODE FOR CARRYING OUT THE INVENTION

The best mode for carrying out this invention will be explained. As shown in Formula I, a methyl ester of a fatty acid and glycerol is to be formed by the transesterification reaction of a fat or oil, which is a triglyceride, and methanol in the presence of a base catalyst.

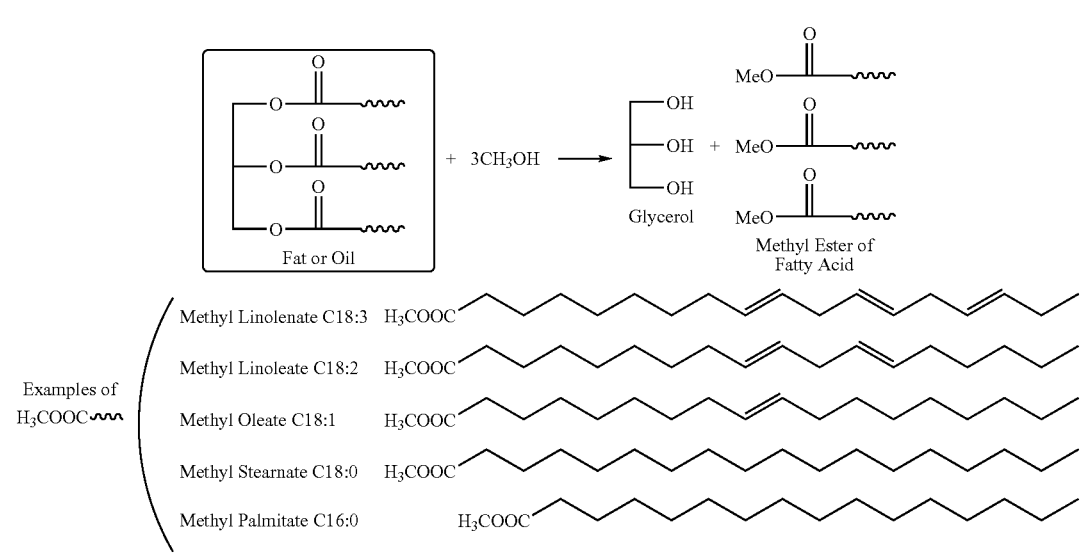

[Formula 1]

The fats and oils to be used as raw materials include, for example, natural vegetable fats and oils such as rapeseed oil, soybean oil, sunflower oil, palm oil, sesame oil, corn oil, coconut oil, safflower oil, cottonseed oil, and castor oil; and animal fats and oils such as beef tallow, lard, and fish oil. In addition, the fats and oils include waste edible oils discarded from restaurants, food factories, households, and the like. In order to carry out the transesterification reaction at a high yield, it is preferable to use a fat or oil of which water content, solid content, and an acidic substance are low. Therefore, if, for example, a waste edible oil is used as a raw material, it is preferable that the waste edible oil is subjected to a pretreatment for removing the water and solid contained. In addition, in a case where an acidic component is contained in a large amount, deacidification, or esterification of a fatty acid by an acid catalyst such as an ion exchange resin, may be carried out as a pretreatment.

The alcohol used in the present invention is not particularly limited. The alcohol is preferably an alcohol having a hydrocarbon backbone having 1 to 5 carbon atoms, and includes, for example, methanol, ethanol, propanol, isopropyl alcohol, butanol, t-butyl alcohol, pentanol, and the like. Further, in the activation of the base catalyst, ethylene glycol, glycerol, or the like besides those mentioned above can be used. Especially, methanol is more preferred, from the viewpoint of being industrially low costs and being easily collected.

As the base catalyst in the present invention, one that promotes a transesterification reaction is used as a solid catalyst, and an alkaline earth metal and oxides thereof, hydroxides thereof, and hydrides thereof can be used. Calcium oxide is most preferred from the viewpoint of its reactivity and costs. As the form of calcium oxide, those catalysts that are in a powdery or granular form, those catalysts supported by various carriers made of zirconia, titania, or ceramic honeycomb, or the like, or those catalysts that are pelletized with resin and carbon materials can be used. Since these catalysts are solid, a risk of admixture of the catalyst into the reaction liquid mixture is markedly reduced, thereby facilitating the separation and collection of the catalyst and the purification of the formed product after the termination of the reaction. Here, ones in a powdery form refer to those having a size that enables sufficient mixing of a fat or oil, an alcohol, and a solid catalyst with a stirrer in a tank reactor or the like, and, for example, a commercially available powdery calcium oxide can be used. On the other hand, since the catalyst is filled in a tubular reactor, those in a granular form must have a sufficiently large size to be held with a holding means such as mesh, so as not to flow through the reaction tube. If the particle size is too large, the reaction efficiency is lowered, and if the particle size is too small, the pressure loss becomes large. Therefore, the particle size, which is properly selected by considering the size of the reaction tube or the like, and the particle size is preferably from 1 to 10 mm, and more preferably from 3 to 8 mm.

The method includes the step of contacting a base catalyst with an alcohol to carry out an activation treatment thereof in advance of the reaction, and this step will be explained. The activation of the base catalyst with the alcohol can be carried out by stirring the base catalyst in the alcohol, or allowing the base catalyst to stand in the alcohol. The temperature for the activation can be from 5° C. to nearly a boiling point of the alcohol. The temperature of 20° to 40° C. or so is preferred because much time is required at lower temperatures, and energy loads are increased at higher temperatures. In a case where a powdery catalyst is used, a base catalyst and an alcohol are filled in a reactor in amounts necessary for the reaction, the components are stirred for 15 minutes to 24 hours, and more preferably from 15 minutes to 5 hours to carry out the activation, and thereafter, a fat or oil raw material is fed thereinto. When a granular catalyst is used in a tubular reactor or the like, a given amount of the catalyst is immersed in the alcohol for 3 to 10 days, and more preferably from 3 to 7 days to allow swelling to carry out the activation, and the activated catalyst is used by filling in the reaction tube. Alternatively, in this case, it is possible that a catalyst is filled together with a cushioning material in the reaction tube from the beginning of the reaction, and an alcohol is filled in the reaction tube, to carry out the activation in the reaction tube.

The reaction conditions for the transesterification reaction will be explained. In a case where a powdery catalyst is used, it is preferable that 3.1 to 14 mol of an alcohol is used relative to 1 mol of a fat or oil, and in consideration of the reaction activity and the removal of alcohol after the reaction, the alcohol is more preferably from 3.1 to 8 mol. The amount of the catalyst is preferably from 0.02 to 5% by weight, and more preferably from 0.03 to 2% by weight, based on the fat or oil. In a case where a granular catalyst is used in a flow reactor such as a tubular reactor, a ratio of the flow rates of the fat or oil to the alcohol is preferably from 3.1 to 40 mol of the alcohol, and the ratio of the flow rates is more preferably from 2 to 28 mol, relative to 1 mol of the fat or oil, from the viewpoint of reduction in the influence of glycerol on the catalyst or the like, maintenance of the reaction activity and the post-treatment after the reaction.

As the apparatus used in the present invention, those having tank, tubular and other shapes can be used. The apparatus may be a batch reactor where a reaction product is obtained for every batch, or a continuous reactor where a reaction product is continuously obtained.

FIG. 1 is a schematic view showing a continuous flow reactor. A fat or oil tank 1 and a methanol tank 2 are each provided with a liquid-conveying pump 3, whereby the fat or oil and methanol are independently fed to a first reaction tube 4 while adjusting their flow rates. Here, a mixer (not illustrated in the figure) for sufficiently mixing the fat or oil and the methanol is also provided upstream of the first reactor tube 4. A base catalyst is filled in the inner portion of the first reaction tube 4, and the fat or oil and the methanol are subjected to a transesterification reaction while passing through this first reaction tube 4. A thermostat apparatus (not illustrated in the figure) is provided on an outside of the first reaction tube 4, which serves to keep the first reaction tube 4 at a given temperature. A first separator 5 is provided downstream of the first reaction tube 4, which mainly removes glycerol. In the reactor of FIG. 1, a second reaction tube 6 and a second separator 7 are provided downstream of the first separator 5. Further, a liquid-conveying pump 3 for feeding methanol is also provided, downstream of the first separator 5 from the methanol tank 2. The transesterification reaction is again carried out after the removal of glycerol by the first separator 6, whereby an alkyl ester of a fatty acid having an even higher purity can be produced.

FIG. 2 shows a schematic view showing a batch production apparatus, and the esterification reaction is carried out by allowing the fat or oil and the alcohol to flow through a reaction tube loaded with a base catalyst. A vessel 10 is provided with a stirrer 11. This vessel 10 and a reaction tube 12 are connected in an annular form, in a manner that a liquid inside the vessel 10 flows into the reaction tube 12, and at the same time the liquid flowing through the reactor tube 12 is again returned to the vessel 10. The reactor is further provided with a means of adjusting the temperatures of the vessel 10 and the reaction tube 12, but not illustrated in the figure.

The reaction tube 12 is loaded with a granular base catalyst subjected to an activation treatment including the step of immersing the base catalyst in methanol in advance of the reaction. The transesterification is carried out by repeatedly allowing the fat or oil and the methanol for one batch portion fed to the vessel 10 to flow through the reaction tube 12 while homogeneously mixing the components in the vessel 10 with a stirrer 11. A by-product glycerol is removed from the vessel 10 as occasion demands. The reactor is stopped when a given purity is attained, and the synthesized alkyl ester of a fatty acid is collected from the vessel 10. The fat or oil and methanol for the next batch portion are introduced into the vessel 10 to carry out the next production.

EMBODIMENT 1

A first embodiment of this invention will be explained. The first embodiment is an embodiment where a batch reaction was carried out with a tank reactor. FIG. 3 is a graph showing the change with time in an yield of an ester (expressed by percentage of weight ratio of a methyl ester of a fatty acid in a reaction product sample), showing a comparison between a base catalyst subjected to an activation treatment and a base catalyst without the activation treatment.

CaO 0.01 g without Activation (Shown as "0.01 g" in FIG. 3)

A 50 ml eggplant-shaped flask equipped with a reflux condenser was charged with 0.01 g of calcium oxide as a catalyst, 3.9 g of methanol, 15 g of a salad oil, and the contents were stirred with a magnetic stirrer at a reaction temperature of 60° C. A small amount of the mixture was sampled in order to monitor the progress of the reaction, and methanol was removed under reduced pressure, and an ester layer was separated by centrifugation. About 100 mg of this ester was weighed, and diluted to a volume of 5 ml with isooctane. Thereafter, the amount of the fatty acid ester was quantified by high-performance liquid chromatography (HPLC), and an yield of the ester was obtained by calculating a weight ratio of the methyl ester of a fatty acid to the reaction product fat or oil. As a result, the yield of the ester after 3 hours was (2%), and the yield of the ester after 10 hours was (64%).

CaO 0.01 g with Activation (Shown as "0.01 g with Activation" in FIG. 3)

An eggplant-shaped flask equipped with a reflux condenser was charged with 0.01 g of calcium oxide and 3.9 g of methanol, and the contents were stirred with a magnetic stirrer at room temperature for 1 hour. Thereafter, 15 g of a salad oil was added thereto, and a reflux condenser was attached to the flask, and the contents were stirred at a reaction temperature of 60° C. The progress of the reaction was monitored in the same manner as above. As a result, the yield of the ester after 3 hours was (57%), and the yield of the ester after 10 hours was (83%).

CaO 0.05 g without Activation (Shown as "0.05 g" in FIG. 3)

A test was conducted in the same manner as in the above Ca 0.01 g without activation, except that the amount of calcium oxide was changed to 0.05 g. As a result, the yield of the ester after 3 hours was (5%), and the yield of the ester after 10 hours was (88%).

CaO 0.05 g with Activation (Shown as "0.05 g with Activation" in FIG. 3)

A test was conducted in the same manner as in the above Ca 0.01 g with activation, except that the amount of calcium oxide was changed to 0.05 g. As a result, the yield of the ester after 3 hours was (89%), and the yield of the ester after 10 hours was (87%).

"Ca 0.05 g with activation" and "Ca 0.01 g with activation" are the embodiments of the present invention. As described above, the yield of the ester can be improved by using a base catalyst after activation by mixing the base catalyst calcium oxide with methanol while stirring. Especially, the rate of increase in the yield of the ester is high immediately after the beginning of the reaction, and reaches to nearly 80% in a short period of time. In a conventional transesterification reaction where CaO is used as a base catalyst, the reaction rate is low and an amount of yield of an alkyl ester of a fatty acid that can be purified from a fat or oil is low. By contrast, according to this invention, a high reaction rate and a high yield of an ester can be realized even while being a solid catalyst.

Next, the influence of the activation time on the activation of a catalyst in an embodiment of carrying out a batch reaction with a tank reactor, using a powdery catalyst will be explained. FIG. 4 is a graph showing the change with time in an yield of an ester, showing a comparison among different treatment time for activation of the base catalyst. Although some differences are found in the reaction rates, it can be seen that if an activation treatment is carried out for 0.5 hours or more, a high reaction rate can be obtained as compared to those without the activation. Here, calcium oxide used in this test is a commercially available powdery calcium oxide (Wako Pure Chemical Industries, Ltd.), and it is preferable that the time required for this activation is properly adjusted while matching conditions such as a baking temperature of calcium oxide.

As described in this embodiment, in a case where a powdery base catalyst is used in a tank reactor, it is preferable that an activation treatment including the step of stirring a base catalyst in methanol is carried out. As shown in FIG. 4, it is preferable that the stirring time is 15 minutes to 24 hours or so. Further, in consideration of the relationship between the required time and the effects, the stirring time is more preferably from 15 minutes to 5 hours.

Next, a comparison with a conventional catalyst is shown. A comparative test was conducted using a homogeneous catalyst potassium hydroxide (KOH).

A test was conducted under the same conditions as above except that a catalyst used was 0.01 g of potassium hydroxide. As a result, the yield of the ester after 3 hours was (77%), and the yield of the ester after 10 hours was (77%). In addition, in a case where potassium hydroxide was changed to 0.05 g, the yield of the ester after 3 hours was (91%), and the yield of the ester after 10 hours was (90%). The present invention as described above is by no means inferior to a case where potassium hydroxide was used in the reaction rate and the yield of an ester. FIG. 5 is a graph showing the change with time in an yield of an ester, showing a comparison between a base catalyst subjected to an activation treatment and potassium hydroxide.

In addition, a comparative test was conducted using a calcium alcoholate catalyst. FIG. 6 shows a graph showing the change with time in an yield of an ester, showing a comparison between a base catalyst subjected to an activation treatment and an alcoholate catalyst.

CaO 0.05 g with Activation (Shown as "0.05 g with Activation" in FIG. 6)

An eggplant-shaped flask was charged with 0.05 g of calcium oxide as a catalyst and 3.9 g of methanol, and the contents were stirred with a magnetic stirrer at room temperature for 1 to 1.5 hours. Thereafter, 15 g of a salad oil was added thereto, and a reflux condenser was attached to the flask, and the contents were stirred at a reaction temperature of 60° C. The progress of the reaction was monitored in the same manner as above. As a result, the yield of the ester after 3 hours was (89%), and the yield of the ester after 10 hours was (87%).

CaO 0.005 g with Activation (Shown as "0.005 g with Activation" in FIG. 6)

A test was conducted in the same manner as above, except that calcium oxide as a catalyst was changed to 0.005 g. As a result, the yield of the ester after 3 hours was (75%), and the yield of the ester after 10 hours was (83%).

Ca(OH)(OCH$_3$) 0.05 g without Activation (Shown as "Ca (OH)(OCH$_3$) 0.005 g" in FIG. 6)

One gram of calcium oxide was added to 10 ml of methanol to prepare a slurry, and the slurry was heated under reflux for 5 hours. The resulting mixture was filtered and dried to give a white powder, and used as an alcoholate catalyst Ca(OH) (OCH$_3$). This is a production method also described in Patent Publication 5. Here, the amount which is an equimolar amount to 0.05 g of CaO, namely 0.079 g, was used. Other than the above, the conditions are the same as those of the above CaO 0.01 g without activation. As a result, the yield of the ester after 3 hours was (49%), and the yield of the ester after 10 hours was (89%).

Ca(OCH$_3$)$_2$ 0.005 g without Activation (Shown as "Ca (OCH$_3$)$_2$ 0.005 g" in FIG. 6)

A commercially available alcoholate catalyst Ca(OCH$_3$)$_2$ was used. This catalyst was tested in the same manner as in the above CaO 0.01 g without activation except that the amount of this catalyst was changed to 0.0091 g. As a result, the yield of the ester after 3 hours was (11%), and the yield of the ester after 10 hours was (65%).

It can be seen from the above the effects of the activation of the catalyst of this embodiment are especially high.

EMBODIMENT 2

A second embodiment of this invention will be explained. This is also an example where a batch reaction was carried out with a tank reactor. A reaction was carried out at 60° C. using 15 g of a salad oil as a fat or oil, and methanol as an alcohol. As the base catalyst, one prepared by stirring 0.005 g of calcium oxide in methanol for 1.5 hours to carry out activation was used. A test was conducted by changing a weight ratio of the fat or oil to methanol to the three conditions (100:26), (100:50), and (100:100). In addition, as a comparative example, a test was conducted in the same manner using 0.005 g of potassium hydroxide (KOH). FIG. 7 is a graph showing the change with time in an yield of an ester in the second embodiment.

In a case where calcium oxide is used, a higher reaction rate and a higher yield of an ester are accomplished than those of a case where potassium hydroxide is used in any of the fat or oil/methanol ratios. In addition, in a case where potassium hydroxide is used, if the amount of methanol is large, a high yield of an ester is attained, but a reaction rate at the initial stage of the reaction is low. If the amount of methanol is small, a reaction rate at the initial stage of the reaction is high, but a high yield of an ester is not attained.

EMBODIMENT 3

A third embodiment of this invention will be explained. This is also an example where a batch reaction was carried out with a tank reactor. The first and second embodiments are embodiments where the reaction was carried out only once with a reaction tank, and even in these embodiments, an alkyl ester of a fatty acid of a purity such that an yield of an ester was 80% or more was already obtained. In this embodiment, in order to increase an yield of an ester, a by-product glycerol was removed after a first reaction, and a second reaction was carried out.

An eggplant-shaped flask was charged with 0.5 g of calcium oxide as a catalyst and 19.5 g of methanol, and the contents were stirred with a magnetic stirrer at room temperature for 0.5 hours. Thereafter, 75 g of a salad oil was added thereto, and a reflux condenser was attached to the flask, and the contents were stirred at a reaction temperature of 60° C. for 4 hours. Methanol was removed under reduced pressure from the liquid reaction mixture, and thereafter the mixture was allowed to stand for some time, to allow a glycerol layer to be separated into layers. The liquid reaction mixture after the termination of this first-step reaction had a BDF yield of 91%. Next, in order to carry out a second-step reaction, the eggplant-shaped flask was charged with 0.25 g of calcium oxide and 15 g of methanol, and the mixture was stirred with a magnetic stirrer at room temperature for 0.5 hours, and a liquid reaction mixture in the first-step reaction obtained above was added thereto. A reflux condenser was attached to the flask, and the mixture was stirred at a reaction temperature of 60° C. for 2 hours. The liquid reaction mixture was filtered to remove the catalyst, and methanol was then removed under reduced pressure. The reaction mixture was allowed to stand for some time, to allow a glycerol layer to be separated into layers. The yield of an ester of this liquid reaction mixture was 97%. From the above, an alkyl ester of a fatty acid having a high purity that satisfies international standards and the like required for the BDF could be obtained.

EMBODIMENT 4

A fourth embodiment of this invention will be explained. This is also an example of production using a batch flow reactor shown in FIG. 2. A reaction tube having an inner diameter of 50 mm and a length of 100 mm was filled with about 75 ml of granular calcium oxide, having an average particle size of 3 to 5 mm or so, which had been activated by immersion in methanol for 5 days. The reaction tube was set in a thermostat set at 60° C., and 150 g of an oil and 50 g of methanol were mixed in a reaction tank, and the mixture was allowed to flow through the reaction tube with a metering pump so as to have a flow rate of 15 ml/minute. After 4 to 6 hours passed, a small amount was sampled, methanol was removed therefrom under reduced pressure, and mixture was centrifuged to separate an ester layer. About 100 mg of this ester was weighed, and an yield of an ester was obtained in the same manner as in EMBODIMENT 1. FIG. 8 is a graph showing a change in catalytic activity by the number of reactions. The yield of an ester was not found to be lowered even when the reactions were repeated 40 times.

An example where an alkyl ester of a fatty acid obtained by separating and removing the glycerol formed by the transesterification reaction was purified by vacuum distillation will also be explained. FIG. 9 is a block diagram showing the constitution of an apparatus for producing an alkyl ester of a fatty acid. A reactor 20 may be a flow reactor as shown in FIG. 1, or a batch reactor (including a batch flow reactor) as shown in FIG. 2. In the case of a flow reactor, a second reaction tube 6 or a second separator 7 may be omitted. A vacuum distiller 21 is provided for subjecting an alkyl ester of a fatty acid formed by this reactor 20 to vacuum distillation.

The distillation is carried out at a temperature of 250° C. or less and a pressure of 10 Torr (1330 Pa) or less. Here, 101 g of an alkyl ester of a fatty acid obtained in this embodiment was purified by carrying out vacuum distillation at a temperature of 160° C. and a pressure of 80 Pa. The data for the purified product are shown in Table 1. It can be confirmed that BDF having high purity was obtained. EU standard values for BDF regarding glycerol, diglyceride, and monoglyceride contents and the like are also shown therein. This purified product has sufficiently cleared all of the standard values, even though it was not easy to clear the numerical figures by the conventional alkali catalyst method. While a BDF having high purity could be obtained as described above, the production costs can be reduced to a low level, and can be also carried out less expensively than a conventional method using a liquid catalyst and a water rinsing treatment.

TABLE 1

| | Ca Conc. ppm | Glycerol % | Monoglyceride % | Diglyceride % | Acid Value mgKOH/g |
|---|---|---|---|---|---|
| Standard Values | 5 | 0.02 | 0.8 | 0.2 | 0.5 |
| Purified Products | 0.7 | 0.007 | 0.01 | 0.0 | 0.14 |

EMBODIMENT 5

A fifth embodiment of this invention will be explained. This is an example of continuous production using a tubular flow reactor. An apparatus as shown in FIG. 1 can be used, except that in this embodiment, an alkyl ester of a fatty acid was produced in a one-step reaction, without using a second reaction tube 6 and a second separator 7. A tubular reactor having an inner diameter of 9 mm and a length of 250 mm was filled with 15 ml of a solid base catalyst activated by immersing about 6.3 g of granular calcium oxide having an average particle size of from 3 to 5 mm or so in methanol at 25° C. for a period of given number of days. A reaction tube was set in a thermostat at 60° C., the mixture was allowed to flow through the reaction tube with a metering pump so as to have a weight ratio of the oil to methanol of 100:75, and a flow rate of 15 ml/hour. In order to monitor the progress of the reaction, a small amount was sampled, methanol was removed therefrom under reduced pressure, and mixture was centrifuged to separate an ester layer. About 100 mg of this ester was weighed, and the ester was diluted to a volume of 5 ml of isooctane, and thereafter an amount of the fatty acid ester was quantified by high-performance liquid chromatography (HPLC), and an yield of an ester was obtained. FIG. 10 is a graph showing the change with time in an yield of an ester in this embodiment. The yields of an ester after 45 hours were 88% where the catalyst was immersed for 5 days, 62% where the catalyst was immersed in 7 days, and 58% where the catalyst was immersed for 5 days.

As described in this embodiment, in a case where a base catalyst is filled in a reaction tube, and a fat or oil and an alcohol are allowed to flow through the reaction tube to carry out a reaction, it is preferable that a granular base catalyst is filled in the reaction tube. In this case, if a base catalyst is loaded to a reaction tube without being immersed in an alcohol in advance, when a fat or oil and an alcohol are introduced into the reaction tube, the base catalyst is swelled up, thereby causing an increase in an internal pressure of the reaction tube, whereas this increase can be prevented by immersing the base catalyst in an alcohol in advance, whereby the performance of the catalyst can be increased. Although the immersion time depends upon the shape of the catalyst or its surface area, or the like, generally the base catalyst may be preferably allowed to stand for 3 days or more, and more preferably 3 to 7 days. Under the conditions of this embodiment, 5 days or so was optimal.

FIG. 11 is a graph showing the change with time in an yield of an ester, showing a comparison among different weight ratios of a fat or oil to methanol. A transesterification reaction was carried out at 60° C. using a base catalyst activated by immersing calcium oxide in methanol for 5 days. Examples of cases where the weight ratios were (100:26), (100:100), (100:150) are shown. If the weight ratio of the fat or oil to methanol is 100:26, an yield of an ester is lowered with the passage of time, and it is preferable that the weight ratio of methanol is 30 or more relative to 100 of the fat or oil, from the viewpoint of the yield of an ester. On the other hand, if the content of methanol is larger, an yield of an ester is found to be lowered, and at the same time the load of treatment for the removal of methanol after the transesterification would be large. From this viewpoint, it is preferable that the weight ratio of methanol is 110 or less, relative to 100 the fat or oil. Those having the optimal balance of the yield of ethanol and the loads of treatment for the removal of methanol have a weight ratio of methanol of 40 or more and 80 or less, relative to 100 of the fat or oil.

INDUSTRIAL APPLICABILITY

This invention can be widely used as a method for producing an alkyl ester of a fatty acid having a small amount of impurities at low costs. Since a vegetable fat or oil can be used as a raw material, this invention can be utilized in, for example, a method for producing a BDF which is a substitute for a fossil fuel. Especially, if a waste oil is used as a raw material, the invention also has a significance in the reuse of waste products.

The invention claimed is:

1. A method for producing a methyl ester of a fatty acid comprising:
    contacting a base catalyst with methanol at 20° C. to 40° C. for 3 days to 7 days, to carry out an activation treatment thereof in advance of a transesterification reaction;
    carrying out the transesterification reaction between a fat or oil and methanol in the presence of the base catalyst containing calcium oxide, wherein the base catalyst is a granular calcium oxide having a particle size of 1 to 10 mm.

2. The method for producing a methyl ester of a fatty acid according to claim 1, wherein the method further comprises:
    mixing the fat or oil and methanol in a weight ratio of from 100:30 to 100:110, and
    allowing a resulting liquid mixture to flow through a reaction tube filled with the granular calcium oxide subjected to the activation treatment by a contact with methanol to carry out the transesterification reaction.

3. The method for producing a methyl ester of a fatty acid according to claim 1, wherein the method further comprises:
    mixing the fat or oil and methanol,
    allowing a resulting liquid mixture to flow through a reaction tube filled with the granular calcium oxide subjected to the activation treatment by a contact with methanol to carry out the transesterification reaction,
    separating glycerol from the reaction mixture, and
    subjecting the resulting mixture to vacuum distillation at a temperature of 250° C. or less and a pressure of 1330 Pa or less to purify the formed methyl ester of a fatty acid.

4. An apparatus for producing a methyl ester of a fatty acid comprising:
    a mixer for mixing a fat or oil and methanol;
    a reaction tube to be filled with a granular calcium oxide having a particle size of 1 to 10 mm subjected to an activation treatment by a contact with methanol of 20° C. to 40° C. for 3 days to 7 days, for carrying out a transesterification reaction comprising allowing a liquid mixture to flow through the reaction tube;
    a separator for separating glycerol from a reaction mixture; and
    a vacuum distiller for purifying the formed methyl ester of a fatty acid.

* * * * *